United States Patent [19]
Lawrence et al.

[11] Patent Number: 5,911,222
[45] Date of Patent: *Jun. 15, 1999

[54] LIQUID REMOVAL SYSTEM

[75] Inventors: W. Thompson Lawrence, Arlington; Clair L. Strohl, Jr., Norfolk, both of Mass.

[73] Assignee: Bristol-Myers Squibb, New York, N.Y.

[ * ] Notice: This patent is subject to a terminal disclaimer.

[21] Appl. No.: 08/730,589

[22] Filed: Oct. 15, 1996

Related U.S. Application Data

[62] Division of application No. 07/927,197, Aug. 7, 1992, Pat. No. 5,678,564.

[51] Int. Cl.$^6$ ..................................................... A61B 5/00
[52] U.S. Cl. ......................... 128/761; 128/760; 128/765; 604/313; 604/317; 604/329; 604/331
[58] Field of Search ...................... 604/347, 327, 604/329, 355, 48.54, 55.73, 378, 313, 331, 317; 120/761, 760, 765; 4/144.1, 144.3

[56] References Cited

U.S. PATENT DOCUMENTS

| | | |
|---|---|---|
| 3,349,768 | 10/1967 | Keane . |
| 4,202,058 | 5/1980 | Anderson . |
| 4,246,901 | 1/1981 | Michaud . |
| 4,360,015 | 11/1982 | Mayer . |
| 4,528,703 | 7/1985 | Krause . |
| 4,589,280 | 5/1986 | Carter . |
| 4,610,675 | 9/1986 | Triunfol . |
| 4,747,166 | 5/1988 | Kuntz ................................. 604/329 X |
| 4,795,449 | 1/1989 | Schneider et al. . |
| 4,798,603 | 1/1989 | Meyer et al. . |
| 4,980,297 | 12/1990 | Haynes et al. . |
| 4,981,474 | 1/1991 | Boop et al. . |
| 5,002,541 | 3/1991 | Conkling et al. . |
| 5,024,653 | 6/1991 | Kohnke . |
| 5,045,075 | 9/1991 | Ersek . |

*Primary Examiner*—Wynn Wood Coggins
*Assistant Examiner*—N. Kent Gring
*Attorney, Agent, or Firm*—Thomas A. O'Rourke

[57] ABSTRACT

A liquid removal system having an interface device and a vacuum source are described. The interface device has a porous membrane with an entrance zone on one side. The vacuum source maintains a vacuum on the side of the membrane opposite the entrance zone when the membrane is wetted. Liquid which contacts the wetted porous membrane is removed from the interface device by the vacuum source.

29 Claims, 14 Drawing Sheets

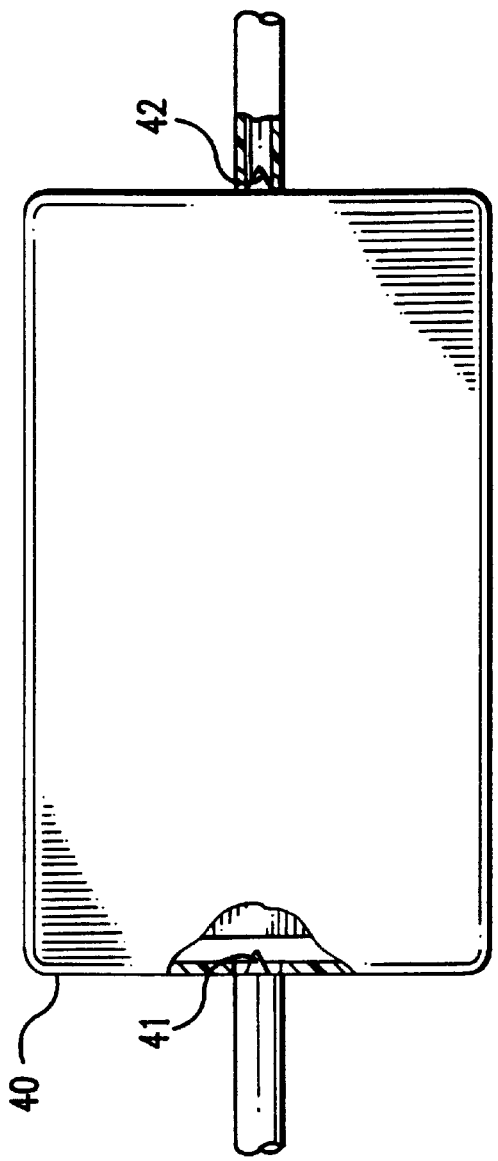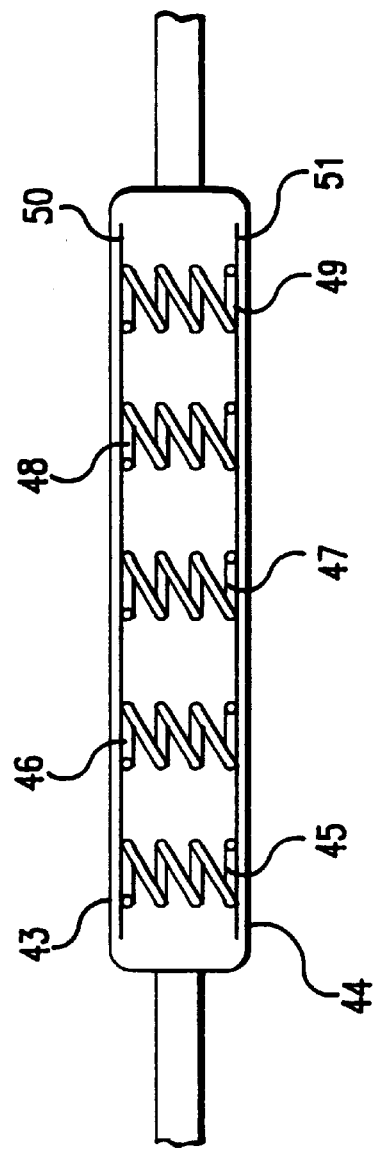
FIG.5a
FIG.5b

LIQUID REMOVAL SYSTEM

This is a divisional of application Ser. No. 07/927,197 filed Aug. 7, 1992 now U.S. Pat. No. 5,678,564.

The present invention is directed toward apparatus and systems used in applications where there is a need for liquid removal. Such applications include laboratories, workshops and elsewhere. Other applications are in the medical and dental fields and include use in wound drainage, chest cavity drainage, oral surgery and others.

The present invention also has particular application as a female external catheter providing improved urine removal to increase patient comfort, to reduce the potential of skin disorders from irritation, and to reduce odors. When used as a female external catheter the present invention has particular applicability to female patients who suffer from incontinence whether they are bed-ridden, have limited mobility or are ambulatory.

BACKGROUND OF THE INVENTION

There are many instances in a laboratory, work shop or other setting where liquid removal is desired. For example, there may be spills or leaks or overflows where it is desired to achieve prompt and relatively effective removal of liquids. While absorbent towels or other conventional means will pick up liquids, there are many instances where it is desirous that the liquid not come into contact with the skin. Thus, there is a need for a liquid removal system which avoids contact with personnel as much as possible.

In the medical area, particularly for wound drainage or chest drainage, there is a need for expeditious and efficient removal of liquid such as blood or other bodily liquid. In view of current concerns over the transmission of communicable diseases through contact with body liquid, there is a need for a system of removing body liquid where personal contact is minimized thereby reducing the risk of disease transmission.

The present invention also has particular applicability in one embodiment as a female external catheter. As the average age of the population in this country increases, a greater number of people are living longer than in the past. The advances in medicine and patient care have contributed greatly to the increased life expectancy. Unfortunately, although there is a greater number of persons who are living to an advanced age, not all these persons are enjoying this benefit through an active lifestyle and have good health. Naturally, there is also an increase of patients who are older but have, for one reason or another, become bed-ridden or have limited mobility due to age or physical disability.

In the past, there was a tendency for families to try, at least initially, to have an older family member reside with them. However, due to various economic and sociological factors this is not always a viable answer to care for the elderly. As a result, there has been an increase in nursing home patients. While some of these patients can care for themselves it will be appreciated that a large number can not readily do so.

Where the patient is ambulatory and has all his or her faculties, the patient can use the bathroom facilities. However, not all of these aged patients, either in the home or nursing home, are ambulatory or have the physical ability any longer to make use of the facilities in a timely fashion. Thus, where the patient is incontinent or bed-ridden or with limited ambulatory abilities, nursing homes and families have been required to use absorbent products such as diapers or indwelling catheters for health or sanitary reasons. Indwelling catheters, however, have the problem of raising the risk of infection.

While diapers do provide increased sanitary benefits for the patient, there are a number of problems that are encountered in their use. First, cloth diapers have laundry costs attributed to them. There is also the sanitary problem of having soiled diapers around before they are disinfected. Disposable diapers while more expensive than cloth are more convenient yet have certain ecological drawbacks. Neither type of diaper, however, is a satisfactory solution because neither the nursing home staff nor the hospital staff can constantly monitor the diaper. As a result, there are times when the patient will be forced to wear soiled diapers before the condition comes to the attention of the staff. Even where the nursing home or hospital has the best of intentions, the facility is frequently short handed on certain shifts and there are, unfortunately, delays in caring for the patient. As a result, with either type of diaper, there are instances where the patient does not receive immediate care in having the diaper removed and replaced with a fresh one. Further, soiled diapers are likely to increase the risk of skin breakdown thereby causing infection and patient discomfort.

In view of the problems with diapers, there have been a number of prior art female external catheters which attempt to solve the problems encountered by bed-ridden patients or patients with limited ambulatory abilities or incontinent female patients. For example, U.S. Pat. No. 3,349,768 to Keane discloses a portable urinal with a suction means and includes an interface unit designed to fit a female human. The interface unit comprises a suction head having the ability therein for receiving a removable pad of an open cell porous material.

U.S. Pat. No. 4,202,058 to Anderson discloses a female urinal comprising a lined shell receptacle having a drainage tube attached. An in-line pump is provided in the tube in the form of a corrugated or cellulose portion with one way valves at each end to provide suction for removing voided urine from the receptacle chamber. Michaued, U.S. Pat. No. 4,246,901 discloses a urine collection device having a generally funnel shaped collecting chamber filled with a wicking material.

A multi-layer absorbent structure or bandage is disclosed in Mayer, U.S. Pat. No. 4,360,015. The absorbent structure of Mayer provides two layers of absorbent material separated by a grid material and covered on one side by a moisture permeable layer and on the other side by an impermeable layer. The upper absorbent layer may be a cellulose material while the lower absorbent layer may be a synthetic cellular sponge. Another absorbent article is disclosed in Meyer, U.S. Pat. No. 4,798,603. This absorbent article comprises a body of substantially hydrophilic material having a facing, liquid permeable top sheet layer of substantially hydrophobic material. A liquid permeable transport layer is positioned between the top sheet and the absorbent body and is made of a material which is less hydrophobic than the body.

Truinfol, U.S. Pat. No. 4,610,675, discloses a device for collecting liquid discharged from females which includes a flexible pad having an elongated central opening for registration with external genitalia. An absorbent core is provided and may comprise a plurality of layers of material.

Martin, U.S. Pat. No. 4,631,061, discloses an automatic urine detecting, collecting and storing device comprising a collection vessel for placement against a person wherein the vessel includes a plurality of sensors for detecting the presence of urine to thereby activate a suction producing means whereby urine is drawn from the vessel to a storage tank.

Kuntz, U.S. Pat. No. 4,747,166 presents a liquid aspiration system for the management of urinary incontinence which includes an absorptive pad for placement adjacent the urinary tract of a patient, the pad having an inner core of urine-absorptive material, an upper pad facing layer of liquid permeable hydrophobic material in contact with the patient and a lower pad backing of impermeable material. The pad encloses a flexible perforated tube having a liquid outlet connector at one end. Also included are a vacuum source, a urine collection vessel and vacuum tubing coupling the tube within the pad to the collection vessel and the vacuum source. The inner core of the pad may be a plurality of layers of absorptive material including cellulose tissue, defiberized wood pulp and expanded cellulose microcellular material.

Kuntz's absorbent pad has a tube at the bottom with a plurality of holes. This tube is in turn connected to a vacuum source during operation, the urine is absorbed into the pad and is then partially removed by the vacuum applied to the bottom of the pad and the body of the absorbent material via the perforated tubing. The vacuum source may run continuously or be activated by a liquid detector in the pad.

An external catheter assembly for women is disclosed in U.S. Pat. No. 4,886,508 to Washington, which includes a panty support for proper placement of the collecting shell. The panty and the shell have cooperating means whereby the shell position can be adjusted relative to the crotch of the panty and the wearer to achieve the optimum location for comfort and function. The panty is also provided with means to adjust for different sized wearers.

Bopp, et al., U.S. Pat. No. 4,981,474, discloses a body liquid drainage device comprising a wedge shaped reservoir having hinged sidewalls joined along a common edge with a collapsible sidewall between them. Spring means are disposed inside the device to urge the hinged sidewalls apart and inlet and outlet ports with at least one way valve are provided for fluid flow.

A device for detecting the pressure of urine at the genital region is disclosed in Conkling, U.S. Pat. No. 5,002,541. The Conkling device includes an external urine collecting vessel which is supported at the genital region to contain the urine within the vessel. Liquid sensors are contained within the vessel for detecting the presence of urine and automatically activating a pump to draw the urine through tubing to a temporary storage chamber. A liquid impermeable liner is provided in the collecting vessel to direct urine away from the user.

Ersek, U.S. Pat. No. 5,045,075 discloses a surgical drain apparatus comprising an elongated drain member and a receiving bag. The bag may be provided with a biasing member to urge the side walls apart following compression thereby producing a negative pressure in the bag and a suction in the drain member.

Kohnke, U.S. Pat. No. 5,024,653 discloses an aspirator comprising a container having a cap shaped member which can be displaced to create a suction in the container and an attached aspirating tube. One embodiment includes a motor and a pivoting arm connected to the cap to provide the displacement thereof.

Thus, while there are a number of prior art attempts to solve the problem of helping patients to remain clean and dry none of these devices are satisfactory solutions.

OBJECTS OF THE INVENTION

It is an object of the present invention to provide an efficient liquid evacuation system that can be used in a myriad of applications where it is desirable to remove liquid such as in laboratories, workshops and in medical and dental facilities.

It is another object of the present invention to provide a liquid extraction system which also has particular application as an external catheter system to replace traditional cloth and disposable diapers and prior art devices.

It is a further object of the present invention to provide a female external catheter system to keep the patient dry at all times thereby preventing skin disorders and reducing odors.

Another object of the present invention is to make care of the incontinent patient easier through the use of an improved female external catheter and thereby permitting the family to care for the patient longer than would otherwise be possible.

Another object of the present invention is to provide a female external catheter system that is less bulky than prior systems or diapers thereby rendering the patient more comfortable than heretofore possible.

A still further object of the invention is to provide a catheter system that permits wheel chair patients to better provide for their needs in public restrooms thereby increasing their mobility.

SUMMARY OF THE INVENTION

The liquid removal system of the present invention is designed to permit efficient liquid removal as needed through the use of an interface device. The interface device is provided with a membrane which has and is capable of maintaining a vacuum on one side so that when liquid contacts the opposite side of the membrane the liquid passes through the membrane and is removed from the interface device by a maintained vacuum to a receptacle for disposal.

When used as a female external catheter system, the present invention is designed to remove urine from incontinent female hospital and nursing home patients and even patients under home care. These patients are usually bedridden or have only limited mobility.

BRIEF DESCRIPTION OF THE DRAWINGS

FIG. 5A depicts a spring vacuum system for use with the interface device.

FIG. 5B depicts a side view of the spring vacuum of FIG. 5A.

DETAILED DESCRIPTION OF THE INVENTION

Figure 2A:
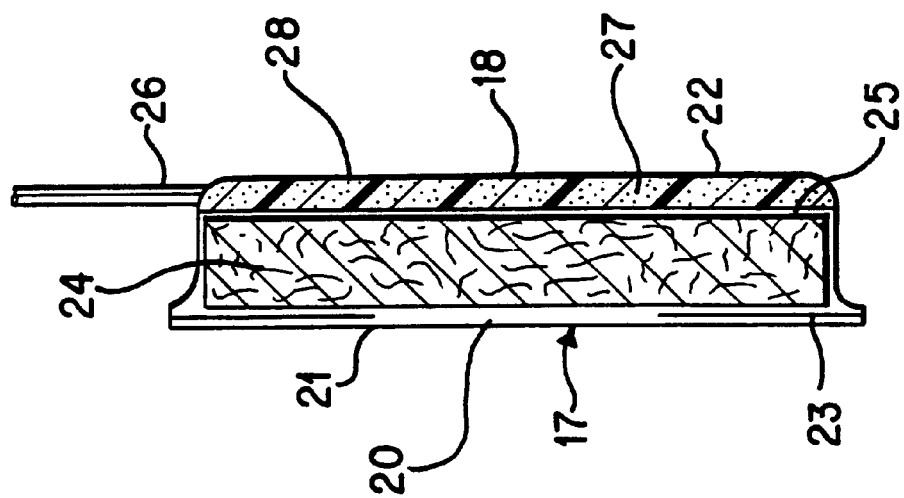
FIG. 2a is a side view of the interface device of FIG. 1.
Figure 1:
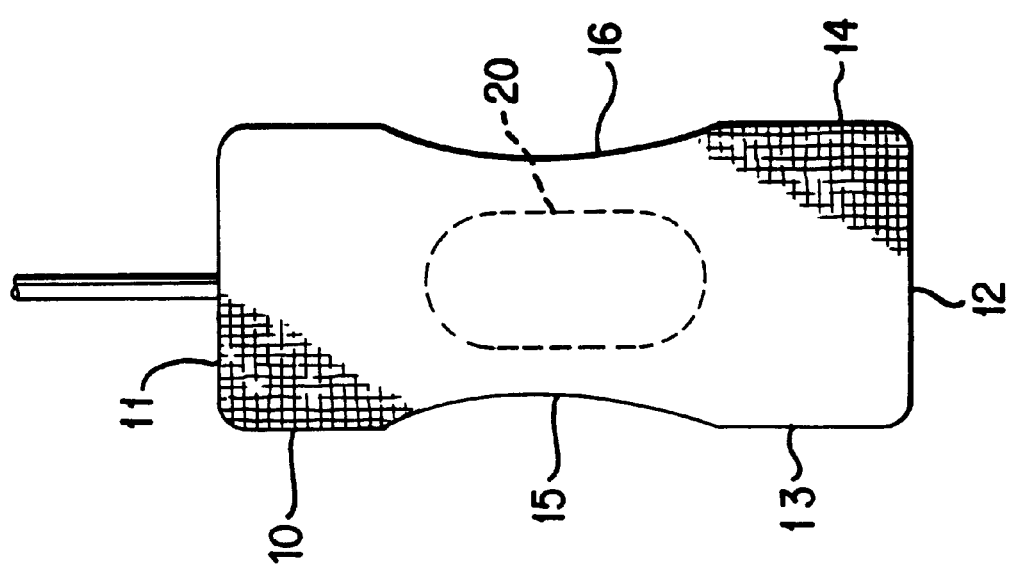
FIG. 1 is a front view of the interface device of the present system.

The external catheter system of the present invention has an interface device 10 which has a generally rectangular shape having an upper edge 11, a lower edge 12 and side edges 13 and 14. Side edges 13 and 14 may be generally parallel to each other or have a design to permit the device to fit in close contact with the body. Cut out areas 15 and 16 which are generally concave in shape are an example of this as they conform to the patient's leg thereby preventing gaps which could cause leakage, or bunched up areas which could cause patient discomfort due to an ill fitting interface device. It will be appreciated by those skilled in the art that other designs or configurations can be used to achieve the same degree of patient comfort. The upper edge 11 of the interface device is positioned toward the front of the patient when worn, while the lower edge 12 is positioned toward the patient's posterior. The interface device may be wider at the back than at the front to aid in urine removal.

The construction of one embodiment of the interface device of the present invention is shown in more detail in FIG. 2a. The interface device is provided with a top or body contact surface 17 and a bottom or external surface 18. The body contact surface 17 is provided with a urine opening which may be generally rectangular, oval, or obround, and of a size and location so as to be aligned with the urethra. The interface device is provided with a coverstock material 21 over body contact surface 17. The coverstock material is preferably hydrophobic (i.e. non-wetting) or treated so that it is rendered hydrophobic. A preferred material for the converstock is a non-woven polymeric fibrous material such as polypropylene which is hydrophobic yet capable of breathing.

The coverstock material is preferably soft against the body to minimize irritation to the patient. Other materials for the coverstock includes suitably treated cotton, rayon, dacron or a cellousic or nylon fiber, in either a woven or non-woven form. The coverstock is capable of repelling moisture but retaining the capacity to "breathe" so that there is a reduced risk of irritation to the skin.

The side of the interface device opposite the body surface side 17 is a plastic shell 28 which is preferably made of a flexible material that permits the device to conform to minor differences in each patient's physique. Between the coverstock and the shell is a impervious layer 23 to which the coverstock is applied. This impervious layer in combination with the shell forms a receptacle in the device for those instances where the flow rate of urine is greater than the evacuation rate of the device. The impervious layer may be a coating on the back of the coverstock material or a separate sheet of polymeric material. The impervious layer may be rendered impervious to liquid by for example flame sealing or a coating with silicone or latex. Alternatively, the coverstock and impervious layer may be laminated in a single layer of material. Any suitable material that is impervious to liquid maybe used. Such materials include polyolefin plastic sheets such as polyethylene or polypropylene including blends thereof. Typical polyethylenes may be low density, linear low density, medium density or high density polyethylene or blends thereof.

A cutout in the coverstock and impervious layer may be used to permit rapid liquid flow to enter the interface device without being diverted to the sides.

The interface device further comprises an entrance zone which may be filled with a fibrous foam or other type filler material 24 such as an open-surfaced, shape retaining material to provide structural stability. This open-surfaced, shape retaining material is a material that permits fluid to flow through it. The device also has a membrane 25 and a drain tube 26 connected to a second volume containing open-surfaced shape retaining material 27. Both the membrane and the drain tube are hermetically sealed to the shell 28. The open-surfaced shape retaining material 27 provides structure to the device and prevents collapse of the device due to the vacuum. In an alternative design (not shown), supporting ribs could be formed into the shell making the use of open-surfaced shape retaining material 27 unnecessary. The foam 24, 27 is preferably an open cell reticulated foam. Preferably, the foam has 10–60 pores per inch (ppi); more preferably about 15–25 ppi. The more pores per inch the more the resistance to liquid flow. A preferred number of pores per inch is about 18–22. Besides a foam or fibrous material, any other type of material would be suitable that permits flow of the liquid to the membrane.

Urine passing through the entrance zone flows into contact with the membrane 25 and is evacuated by suction applied at said membrane 25. The suction is applied to the membrane by a vacuum through the drain tube. The membrane should be firmly attached to the shell with an hermetic seal to maintain the suction.

The material for the filter layer or membrane is preferably hydrophilic and has a pore size on the order of about 5 to about 30 microns, more preferably about 15 to 20 microns. Once the membrane has been wetted it will support a suction pressure of typically about 5 to about 60 inches of water without permitting air to pass. Depending on the size of the pores, the suction pressure that can be applied without air passing through the membrane varies. The smaller the pore size the greater the pressure that may be supported. Thus, if suction is applied to the drain tube and the membrane has been wetted, whenever urine comes in to contact with the membrane it is drawn by the suction through the membrane into the foam and removed through the drain tube. It is preferred that the vacuum be in a range of 5–60 inches of water.

As long as the filter material or membrane remains wet, air does not pass through the filter and suction is maintained without active pumping. If too much vacuum is applied to the membrane there is a risk that the bubble point of the membrane will be surpassed and there will be no liquid in one or more pores of the membrane. In such a situation, the vacuum is lost and liquid will not be removed. Thus the amount of vacuum should approach as close as possible but not exceed the bubble point. Another advantage of the arrangement of the interface device is that the membrane acts like a variable area tube entrance whose area depends on the amount of liquid on the entrance zone side. Consequently, all of the liquid is removed regardless of the orientation of the device such as when the patient is reclining, sitting or standing.

While it is preferred that an open cell foam be used in the interface device other materials can be used. For example fiber material such as a cellulosic material or wood fluff, cotton or other material that is highly absorbent can be used. The filter material or membrane is preferably a woven membrane PES 18/13 sold by Saati or a similar membrane sold by Tetko. Other suitable material having a pore size on the order of about 10–30 microns can also be used.

Figure 2B:
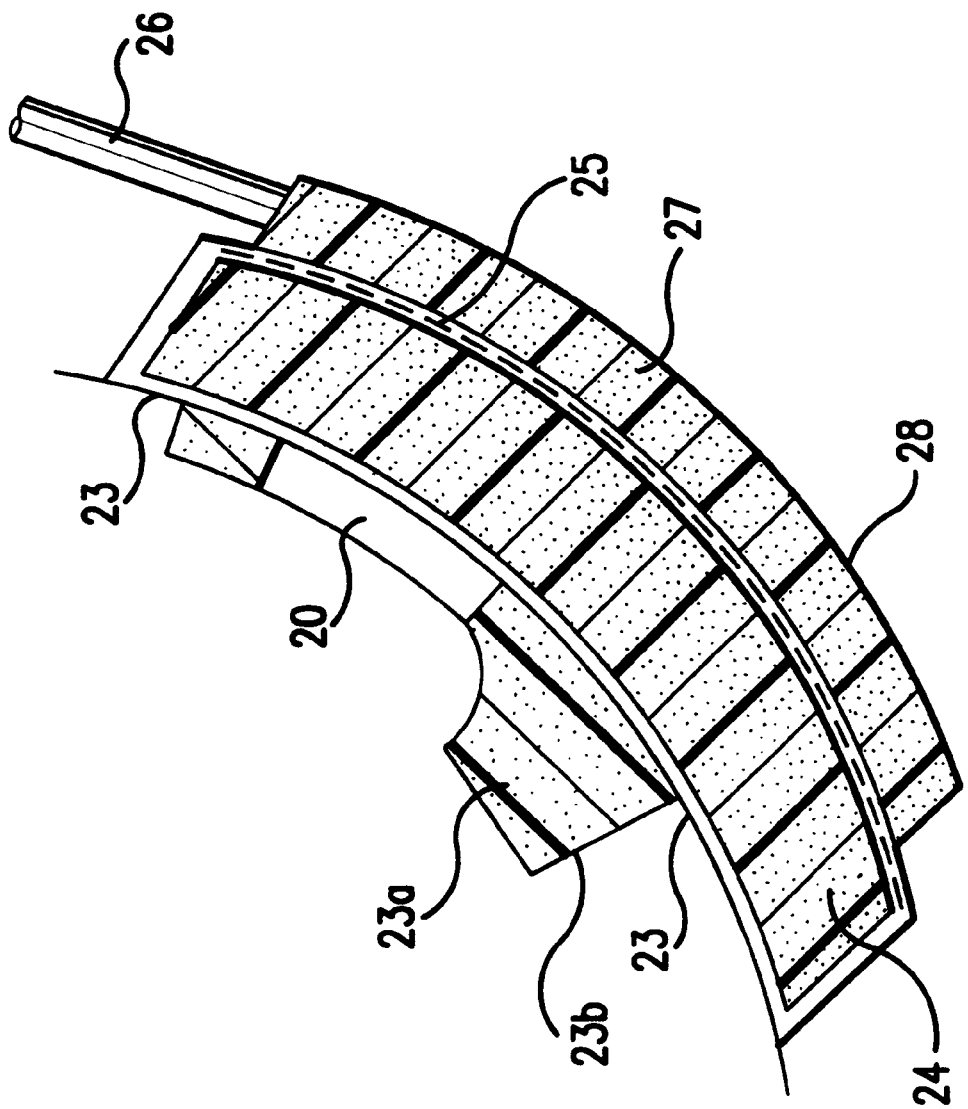
FIG. 2b is a side view of an alternative embodiment of the interface device of FIG. 1.

An alternative embodiment of the invention is shown in FIG. 2b. As seen in FIG. 2b there is an impervious cover 23 with an opening 20 for liquid entry. The impervious cover is modified by attaching an external foam dam 23a which surrounds the opening and provides a method of sealing the device to the wearer thereby preventing the leakage of urine particularly at low flow rates. The external foam dam may have several different features to improve the seal. In the case shown, a bump 23B at the rear is used to seal the device by pressing against the area between the vagina and anus. The foam bump is preferably made from a soft, open cell foam which compress easily but which doesn't pass liquid. It is preferred that the foam dam or bump be comprised of small cells and compressible to seal the area between the anus and the vagina. The seal between the foam dam and the skin is enhanced by the application of a petroleum jelly or a similar sealing material to improve the seal when the patient is reclining.

An example of a foam is Opcell fine (Sentinel Products Corp.) which contains very small pores and thus limits liquid flow but has open cells so that it is very compliant. In order to improve the leak resistance of the interface device of the present invention a raised portion of foam (not shown) may be added under the coverstock to increase the seal properties when the patient is in a reclining position. In this embodiment, two regions of an open celled foam material 24 and 27 are provided on opposite sides of membrane 25. The impervious cover 23 is connected to a shell 28. Outlet tube 26 is provided to evacuate the urine from the interface device.

Figure 3D:
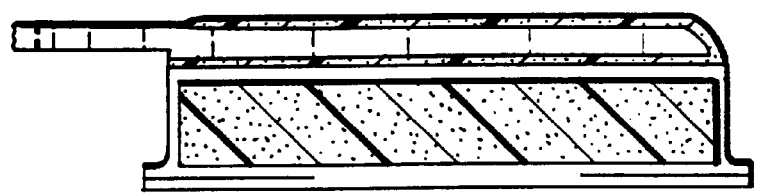
FIG. 3a to 3d depict the operation of the interface device when urine is present.
Figure 3C:
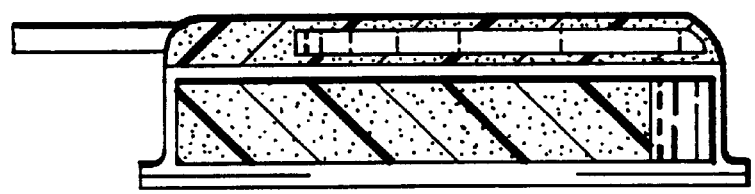
Figure 3B:
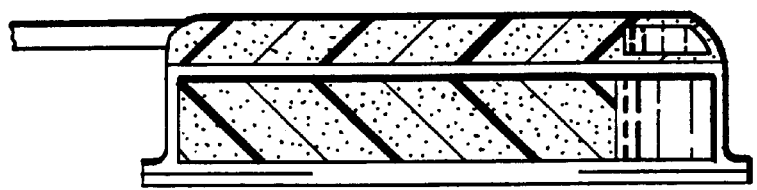
Figure 3A:
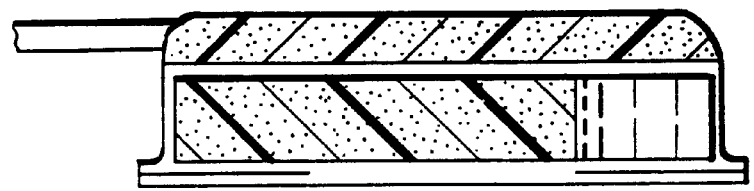

The operation of the interface device is depicted in FIGS. 3a–3d. As shown in FIG. 3a, urine has passed through the urine opening 20 in the coverstock, into the foam material, 24 and collected toward the base of the interface device. As time elapses, the urine is drawn through the membrane into the foam material 27 due to the action of the suction. Continued application of the suction permits the urine to rise to the drain tube thereby evacuating the urine from the foam material 24. It should be borne in mind that the operation of the device as shown in FIG. 3A–D is rapid and the time interval between each stage is very small. In practice this process occurs in less than a second and little or no urine actually collects as shown in FIG. 3A unless the flow rate exceeds approximately 20–25 cc/sec. FIGS. 3A–3D generally depict the operation of the interface device where the patient is in a reclining position. Where the patient is standing or sitting the urine will not necessarily collect in the base of the interface device. Rather the flow will be more uniform against the filter.

As noted above, the ability of the external catheter of the present invention to keep the patients dry is enhanced by the application of a continuous suction force to the drain tube. This may be accomplished by a pump that evacuates air from the system until an appropriate vacuum is reached. At that point the pump shuts down. Because the pores in the membrane are filled with liquid, a vacuum is maintained until liquid reaches the membrane. At that point the liquid is pulled through the membrane by the vacuum and is removed from the system.

An important consideration in a catheter system which is dependent upon a suction type force for removal of urine is how to initiate operation of the system. When manufactured and during storage, the filter material is dry. Until it is wetted, it will not support a vacuum. The nurse, aide or other caretaker could wet it before placing it on a patient but this would require an additional step, and, if it were done incorrectly, the device would not function. To avoid this problem, the filter material can be prewetted during manufacture. This may be done by any suitable liquid having a low vapor pressure. Glycerin is preferred as a prewetting agent because it will not dry out and will support the vacuum until the first wetting with urine. The urine passes though the glycerin wetted filter material with no difficulty and a suction is supported by the glycerin. Once the unit is wetted with urine, the glycerin is washed out, and the urine in conjunction with the membrane supports the vacuum.

It may be appreciated that the continuous suction may be applied by any appropriate source. In one embodiment, shown in FIG. 4, the drain tube is extended and filled with a liquid. The outlet of the tube, which can evacuate into any suitable receptacle such as a conventional bedside collection bag, is positioned so that it is lower than the interface device. Thus, a vacuum will be applied to the interface device which is equal to the height difference between the interface device and the end of the outlet tube. The external catheter system of FIG. 4 would have particular application where the patient is in a bed and the urine collection bag is for example at floor level. It will be appreciated, however, that the system of FIG. 4 would have other applications as well. For example, where a patient is in a wheel chair and the urine receptacle is in a position lower than the patient such as appended to an adjustable retaining means on the wheelchair so that the height can be varied by patient, wheel chair size or other variable. When the membrane has a pore size of 18 microns, the height of the suction head should be approximately 18" in order for the vacuum to be maintained. Other heights will correspond to other pore sizes in a similar fashion as will be appreciated by those skilled in the art.

Figure 4:
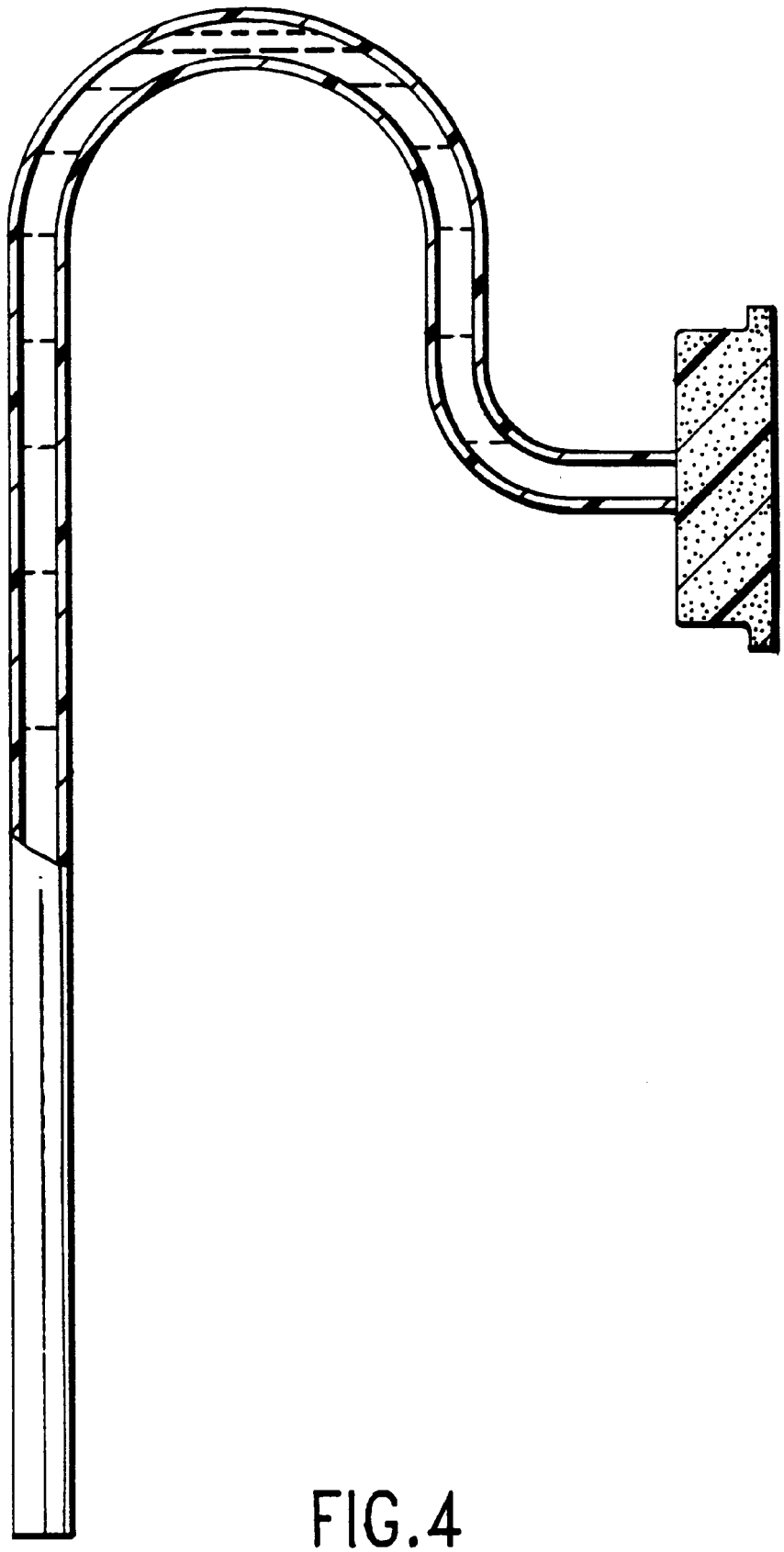
FIG. 4 depicts the interface device with a suction head provided by gravity.

The system of FIG. 4 has the disadvantage that the tube must be initially filled with liquid for that method to work successfully. In addition, whenever the interface device is disconnected from the collection bag, the liquid in the tube will flow into the bag and the device must be refilled with liquid in order to re-establish the suction. This is overcome by using active suction devices preferred embodiments of which are described in detail below.

There are a number of methods for actively maintaining a vacuum. In one preferred embodiment, a conventional leg bag for urine collection has been modified by placing springs inside as shown in FIG. 5B. The leg bag 40 has a pair of check valves 41 and 42. Check valve 41 is an inlet check valve which permits liquid to enter the bag but does not permit the liquid to return to its source back through the check valve. Check valve 42 is an exit valve which prevents air from entering the bag thereby maintaining a vacuum. As shown in FIG. 5B, the leg bag has an upper surface 43 and a lower surface 44. A plurality of springs 45–49 are provided and held in place by a pair of opposing rigid sections 50–51. In operation, the leg bag's sides are pressed together to charge the device and a manual valve (not shown) on the exit is closed. The check valve on the exit prevents air from being drawn back into the bag while the user is closing the manual exit valve. The check valve on the entrance prevents air or urine from being forced back into the interface device. The springs pushing against the sides of the bag generate suction in the device. This is similar to other products used for wound drainage such as that shown in U.S. Pat. No. 4,161,179.

Figure 6:
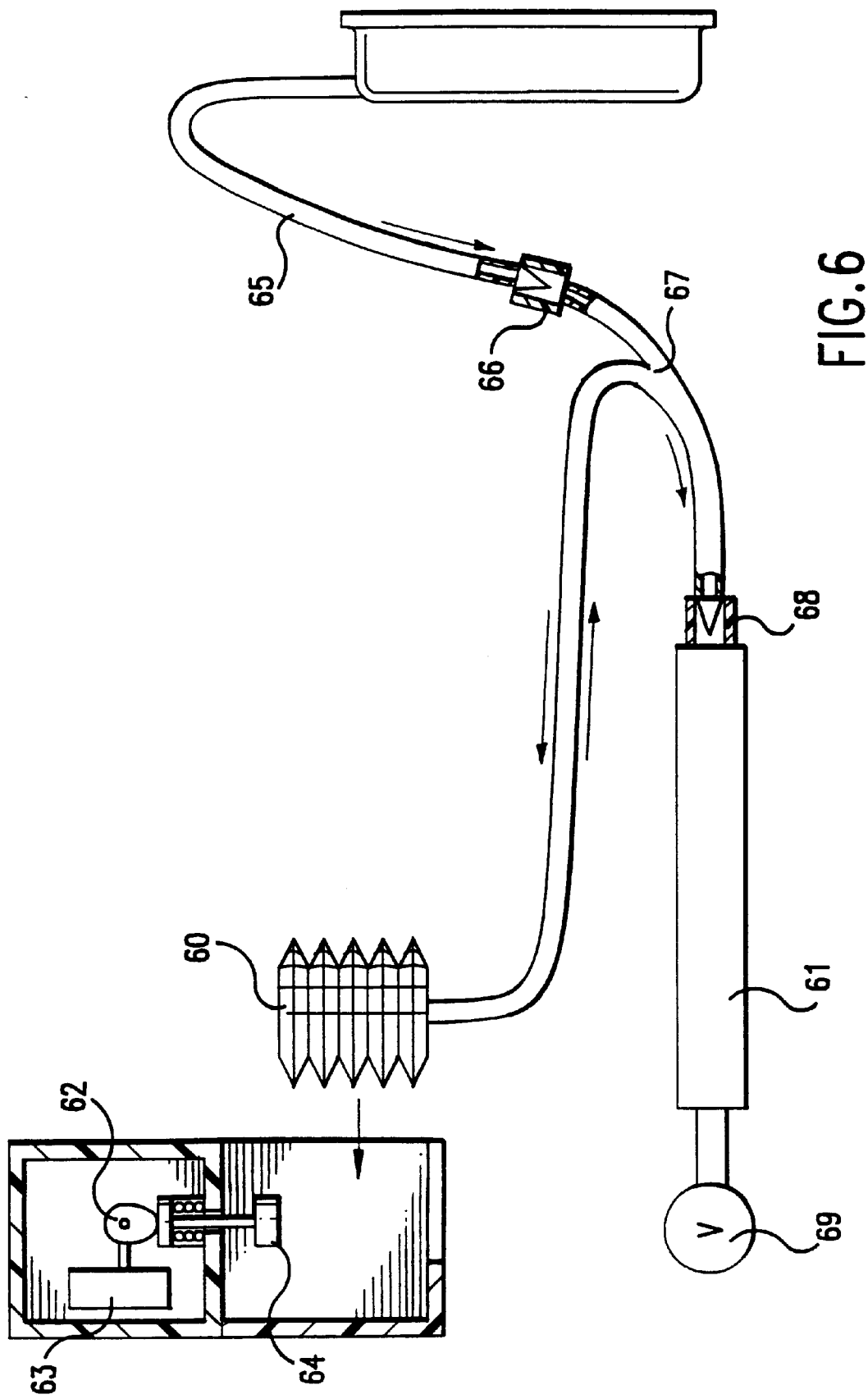
FIG. 6 depicts a pump system of the present invention for use with the interface device.

In an alternative approach, a pump would be used to maintain suction on the interface device. One geometry which offers several advantages over conventional designs is shown in FIG. 6. This method incorporates a plastic, molded bellows 60 in connection with a leg bag 61. The bellows acts as a pump unit. Duck bill valves are positioned in the tubes as shown to permit the bellows to provide a vacuum. The natural spring effect of the bellows depends on the wall thickness and the type of plastic used. The system operates so that this spring force gives the desired suction head. The bellows is compressed by a cam 62 connected to a gearmotor 63. Liquid passes from the interface device through the tubing 65 and passes through a duck bill valve 66. From that duck bill valve the liquid passes through the "T" shaped tubing 67 and thereupon through a second duck bill valve 68 and then into a leg bag 61. The leg bag 61 is provided with a drain valve 69 to remove the liquid.

This design isolates the electrical and mechanical parts of the pump from contact with urine. As the bellows is part of the disposable portion of the apparatus which is discarded every 1 to 2 weeks, no cleaning of the pump unit is needed. The design also lets the pump operate in any attitude and the bag into which the liquid is being pumped also in any position. This combination of features cannot be achieved with conventional designs.

A control means 64 may be used so that the motor runs only when urine is introduced into the interface device and the suction force in the bellows drops to a preselected level. Several means of controlling the motor have been developed. In one such means, switches monitor the location of the bellows and turn the motor on when the bellows is expanded to a preselected size. The switches could be electromechanical or more preferably be electro-optical. In another means a conducting material is attached to the end of the bellows in contact with the piston. The piston is fabricated with two wires passing axially through it with the ends of the wires extended so that they contact the conducting surface in the tubes when the bellows is extended. The pump is wired so that, when the circuit is closed by the contact of the bellows with the piston, the motor turns pumping liquid from the interface device into the bag. When no liquid is present to pump, the bellows does not return after it is compressed by the piston and thus the electrical contact is broken stopping the pump. The natural spring force of the collapsed bellows maintains suction on the interface device. When urine again enters the interface device, the suction is reduced, the bellows expands, touches the piston, and the pump motor starts.

Figure 7:
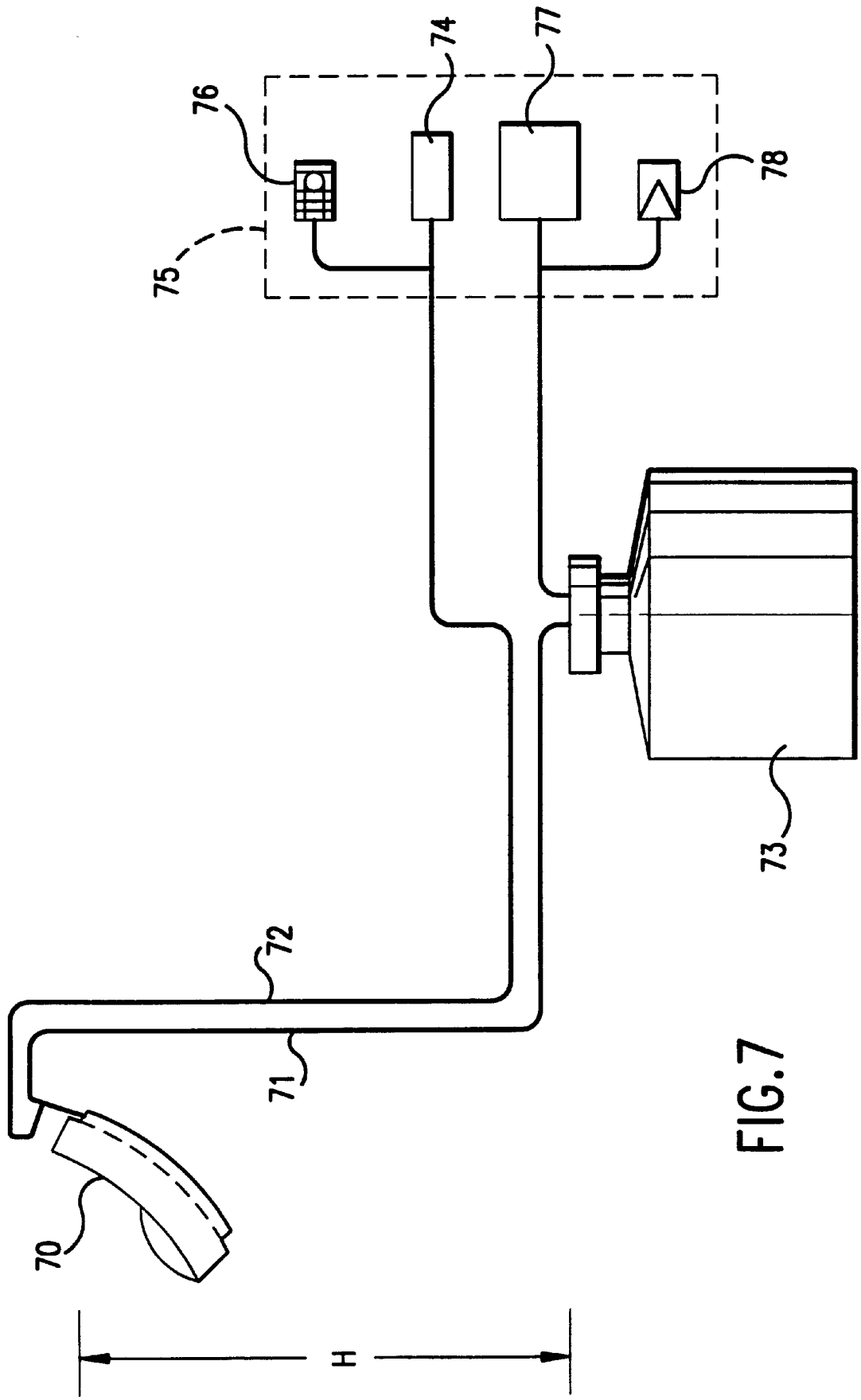
FIG. 7 depicts an alternative embodiment of the pump system of FIG. 6.

FIG. 7 depicts an alternative embodiment of the pump system of the present invention. The pump system of FIG. 7 is designed to permit the use of a membrane with a bubble point as low as 18 inches of $H_2O$. This system provides an interface device 70 with hollow tubing 71 and 72. Tubing 71 is connected to a vacuum bottle 73 while tubing 72 is connected to a pressure transducer 74. The pressure transducer is attached to a secondary line of tubing. When the vacuum reaches a preset value, the motor of the pump stops. When the transducer detects a decrease in vacuum the pump is thereupon activated. A pressure relief valve 76 is provided in tubing 72 and is connected to the line preferably inside the pump housing 75 just before the pressure transducer 74. The pressure relief valve prevents the vacuum from exceeding a preset value. From the vacuum bottle 73 a length of hollow tubing extends to the pump 77. Connected to the tubing is a duck bill valve 78.

The system of FIG. 7 will accommodate various changes in the length H (head). A preferred filter for use in the interface device with this system is Saati PES 18/13 filter. The system of this figure can also provide 30 cc/sec of pumping capacity.

In operation, the vacuum pump provides an initial vacuum head of about 18 inches of $H_2O$ when there is no fluid in the line. If the vacuum exceeds 18 inches of $H_2O$, due to changes in "H" when tubing 71 is filled with liquid, the pressure relief valve permits air to enter the line and reduce the liquid column height to a more acceptable value. In an alternative configuration (not shown), the check valve is replaced with a solenoid valve controlled by the pressure transducer. In this case, when the vacuum exceeds 18 inches of water, the control circuit opens the valve allowing air to enter the line until the vacuum is reduced to an acceptable level, for example 17 inches of water.

The duck bill valve prevents positive pressure in the vacuum bottle if urine flow is too fast. This is not necessary if a high flow pump is used i.e. greater than 30 cc/sec at 18" $H_2O$. The tubing is preferably 0.35 to 0.45 inch measuring the inner diameter. The line to the pressure relief valve is preferably 0.125 inch inner diameter. In order for the system to operative effectively the vacuum bottle is preferably rigid and not flexible.

The pump is intended to operate only when urine is present, and at the start up. This provides longer battery life.

Figure 8:
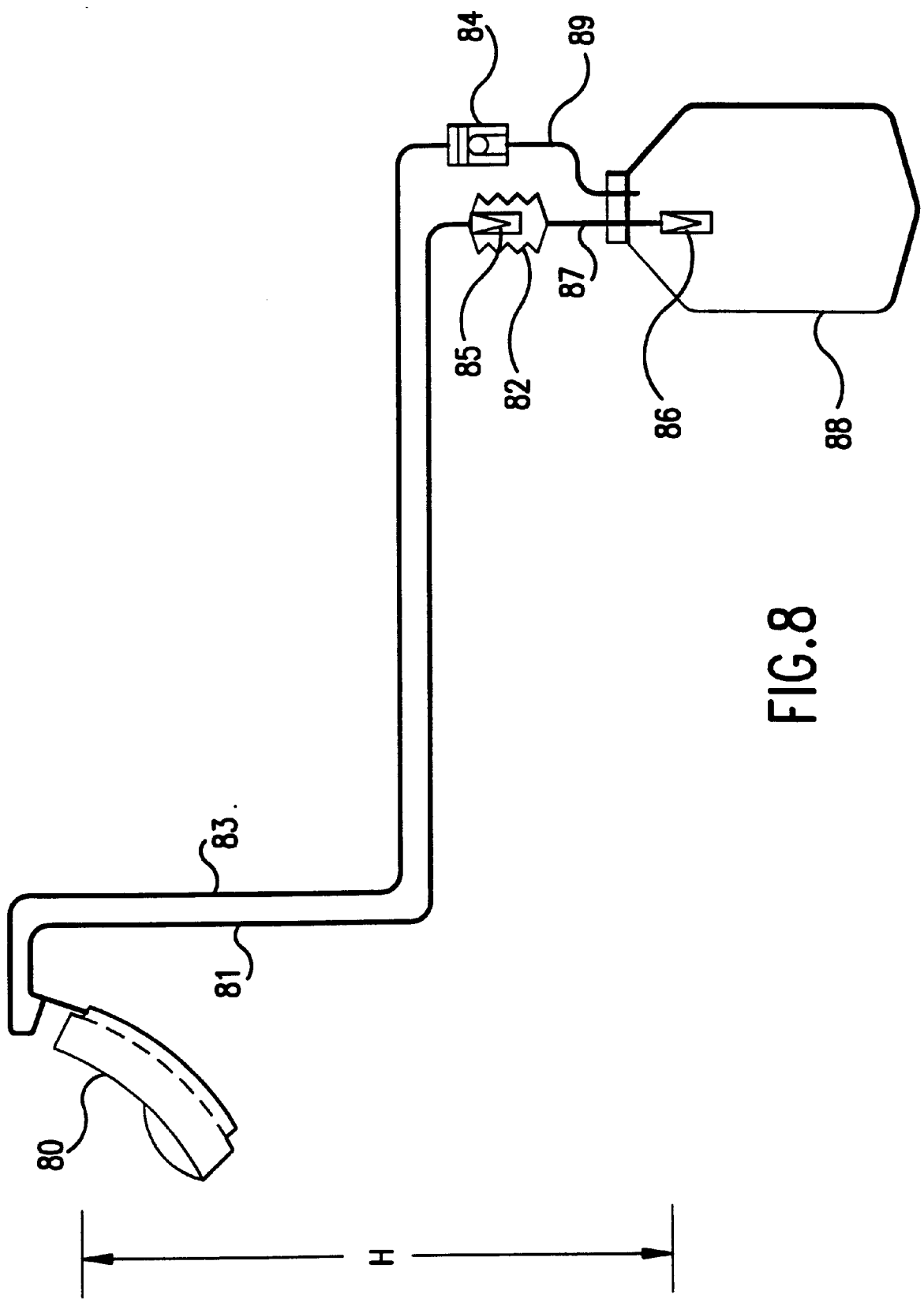
FIG. 8 depicts a gravity passive flow system of the present invention.

FIG. 8 depicts a gravity passive flow system. As shown in FIG. 8 there is provided an interface device 80 with one length of tubing 81 extending from the interface device to a hand pump 82. A second length of tubing 83 extends from the interface device to pressure relief valve 84. The hand pump 82 is provided with a duck bill valve 85. A second duck bill valve 86 is connected to a length of tubing 87 which extends from the pump 82 into the collection bag 88. A length of tubing 89 extends from the pressure relief valve 84 to the collection bag.

In the apparatus of FIG. 8 it is preferred that the collection bag be hung so that "H" is at least 16 inches in height. During operation the hand pump is squeezed several times until it remains collapsed providing suction due to the natural spring force of the bulb. The duck bill valves operate similar to check valves while providing full flow capacity.

When the patient's initial flow of urine fills the tube, head is provided to provide subsequent vacuum. If "H" exceeds 18 inches $H_2O$ pressure the relief opens injecting air and maintaining the liquid column at an acceptable range.

Figure 9A:
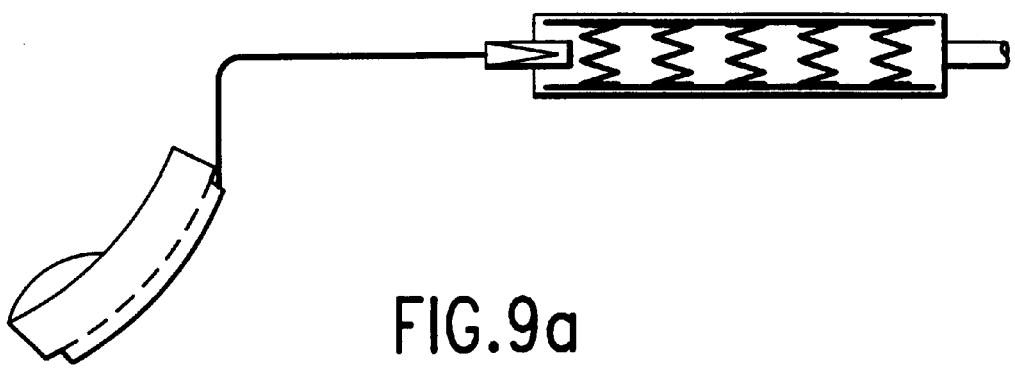
FIG. 9A depicts an arrangement of the present invention using a spring bag system where the patient is sitting.
Figure 9B:
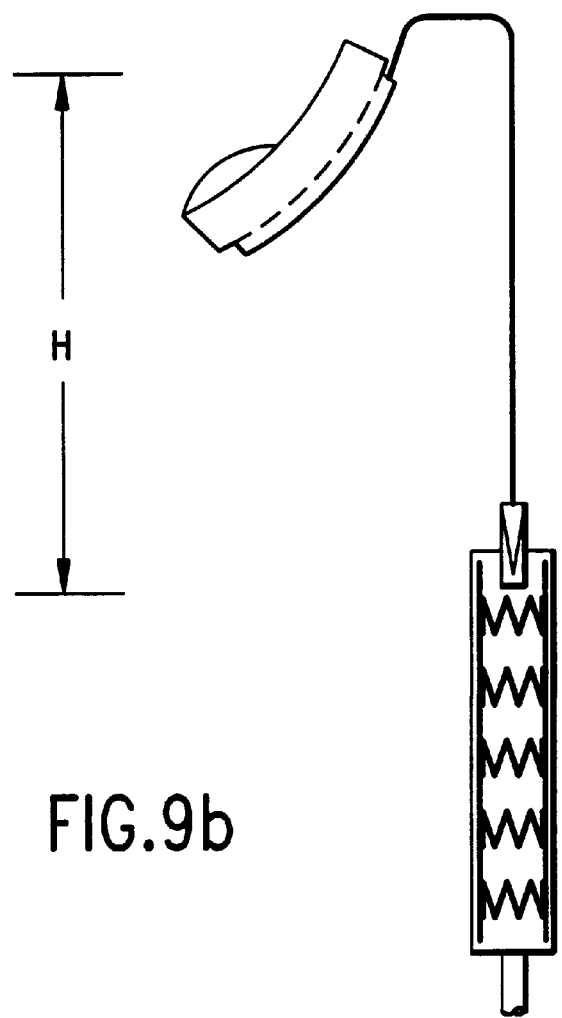
FIG. 9B depicts the spring bag system of FIG. 9A where the patient is standing.

FIG. 9 shows the spring bag apparatus of FIG. 5 showing the arrangement when the patient is standing or reposing. The spring bag apparatus has certain important advantages. It is designed to permit use with a membrane having a bubble point as low as 18 inches of $H_2O$. The device can be worn concealed and can hold a large volume of urine. It has been found that the device of FIG. 9 can hold up to about 400 cc's of urine before emptying. The device can hold more than 400 cc's but can tend to be too bulky. The membrane is preferably a PES 18/13 Saati filter. The device is also able to handle up to 20 cc/sec.

During operation the interface device is placed on the patient. The spring bag is collapsed and sealed. The spring bag is attached to the thigh and can be hidden by clothing. When the patient is standing the suction equals the head "H" plus the spring bag suction. When sitting the bubble point will not be exceeded because the head "H" from the interface device to the duck bill is only 3–5 inches.

Figure 10:
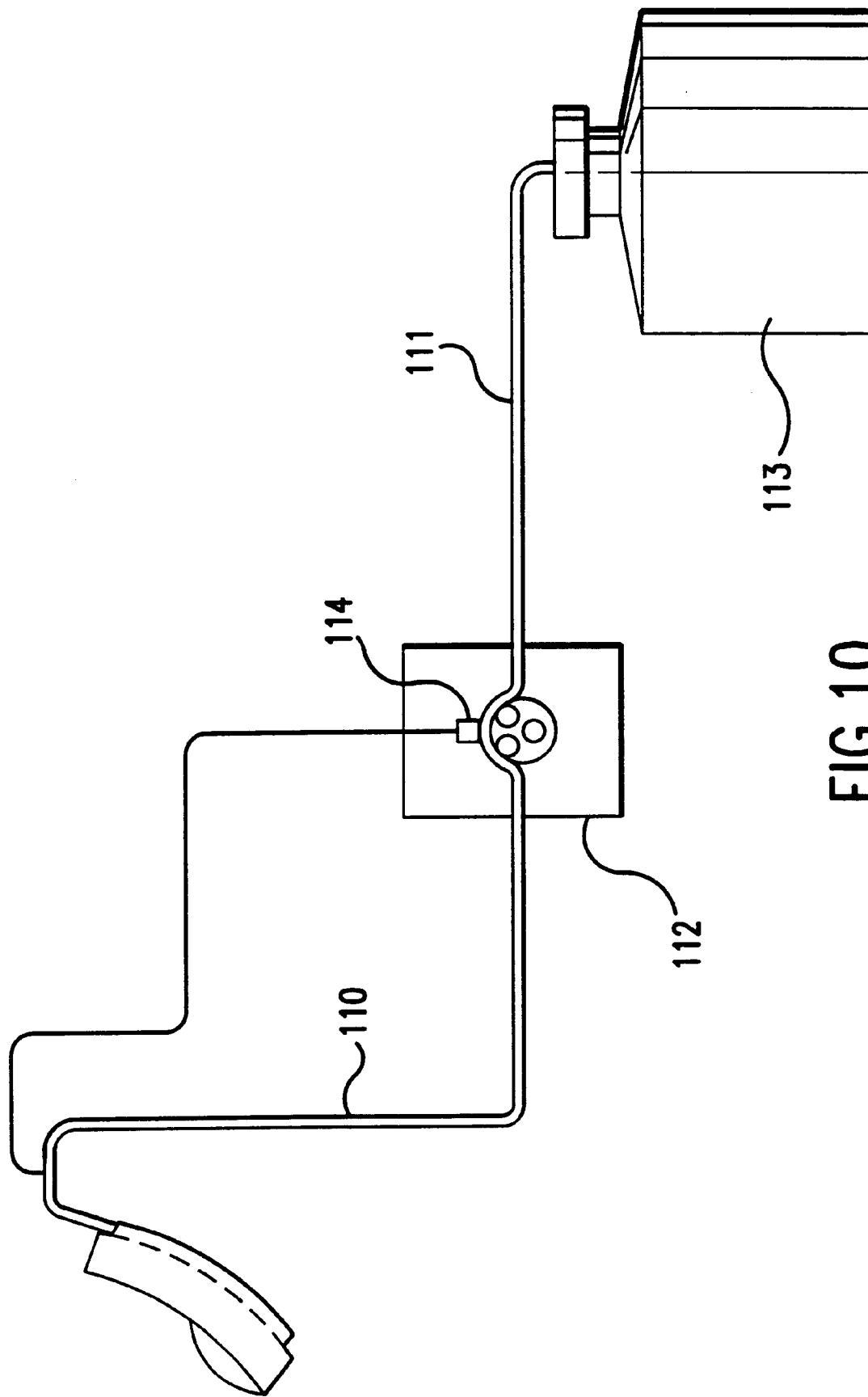
FIG. 10 depicts an alternative embodiment of the system of the present invention where the fluid passes through the pump.

FIG. 10 shows the interface device of the present invention with the tubing 110 being connected to a pump 112 such as a peristalic pump or a pump with a disposable pumphead. The tubing 111 continues from the pump to the receptacle 113. The pump is also provided with a pressure transducer 114 which monitors the vacuum between the interface device and the pump. When the vacuum is reduced, the transducer will cause the pump to become activated increasing the vacuum to the level needed to remove urine at the desired rate.

Figure 11:
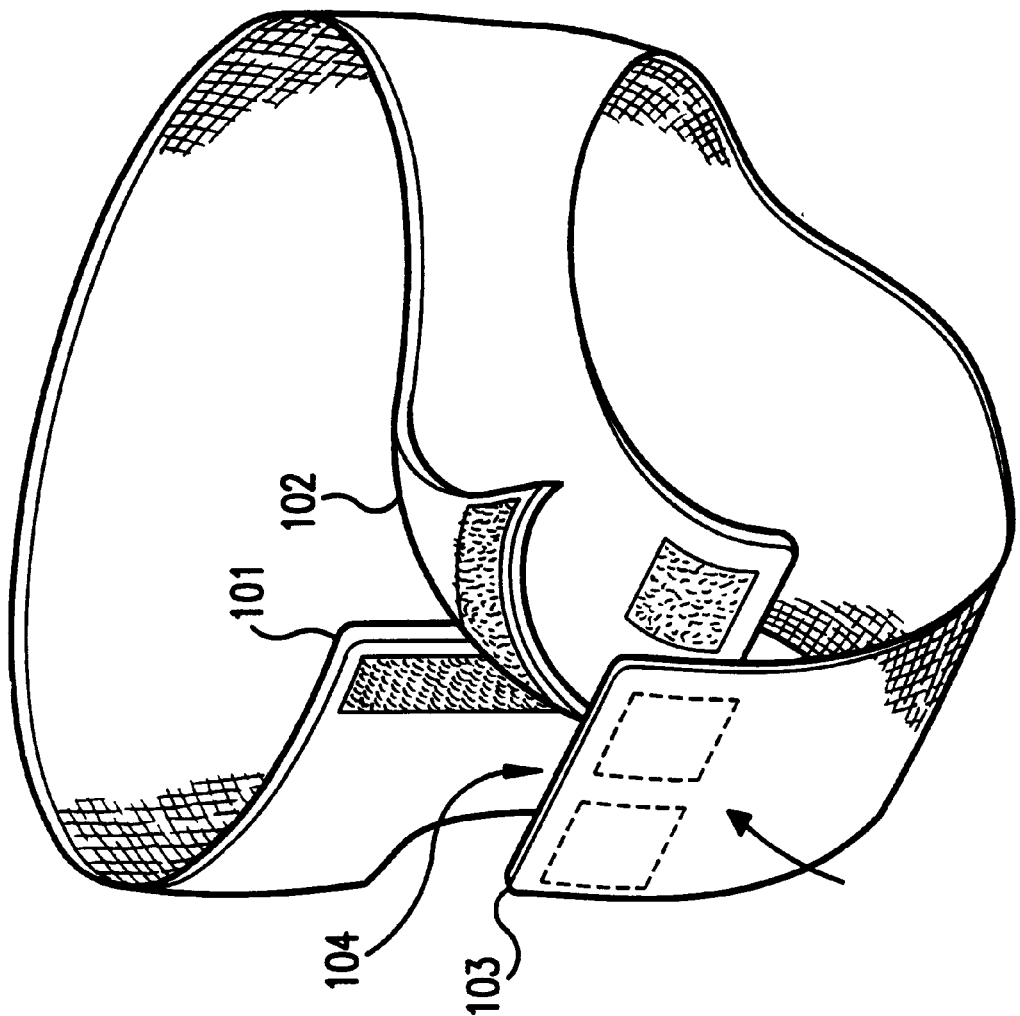
FIG. 11 depicts the brief of the present invention which may be used with the interface device of the present invention.

The interface device is retained in place on the patient with a pants like brief or other suitable retaining means. The support pants or brief, FIG. 11, may be generally "T" shaped in its open configuration. The opposite sides of the "T" 101, 102 can be joined together and fastened to form a waist band with Velcro or other suitable fastening means such as resealable tape, snaps, buttons, etc. The crotch portion is formed by joining the base of the "T" 103 to the waist band in a similar fashion. An area 104 is provided for the tubing of the interface device to pass through the brief. The brief may also be similar to a pair of cotton underpants and can come in different sizes. The brief may also be designed with a belt or straps such as straps made of Velcro at the waist to adjust for different sizes. The brief would be preferably washable or disposable. Besides a brief, a garter belt type of arrangement can also be used to retain the interface device. Furthermore, the brief or other type garment for retaining the interface device in contact with the patent can also have provision for an existing fecal collection system.

Figure 12:
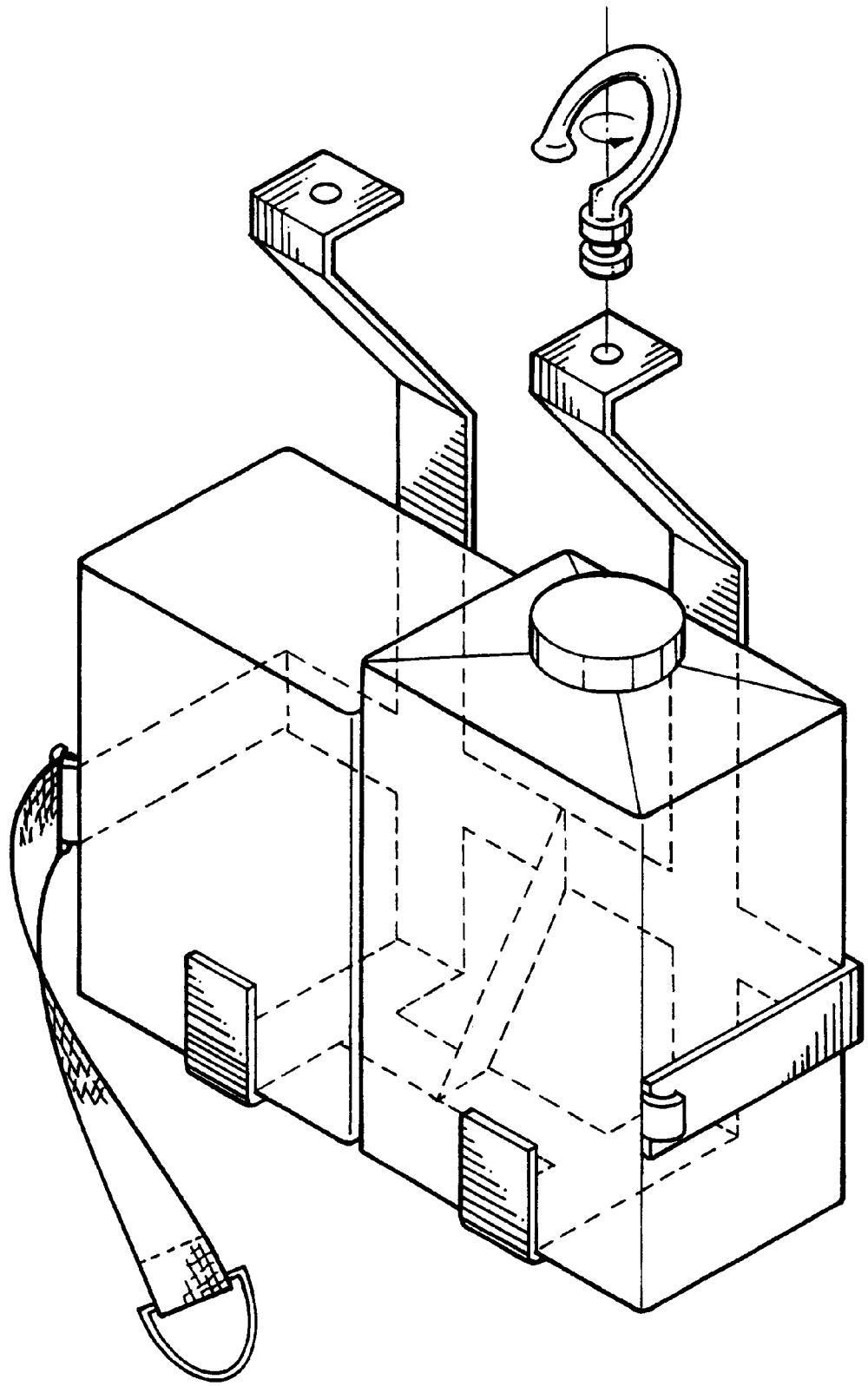
FIG. 12 and 13 depict racks for holding the pumps and liquid receptacle on a bed or a wheelchair.
Figure 13:
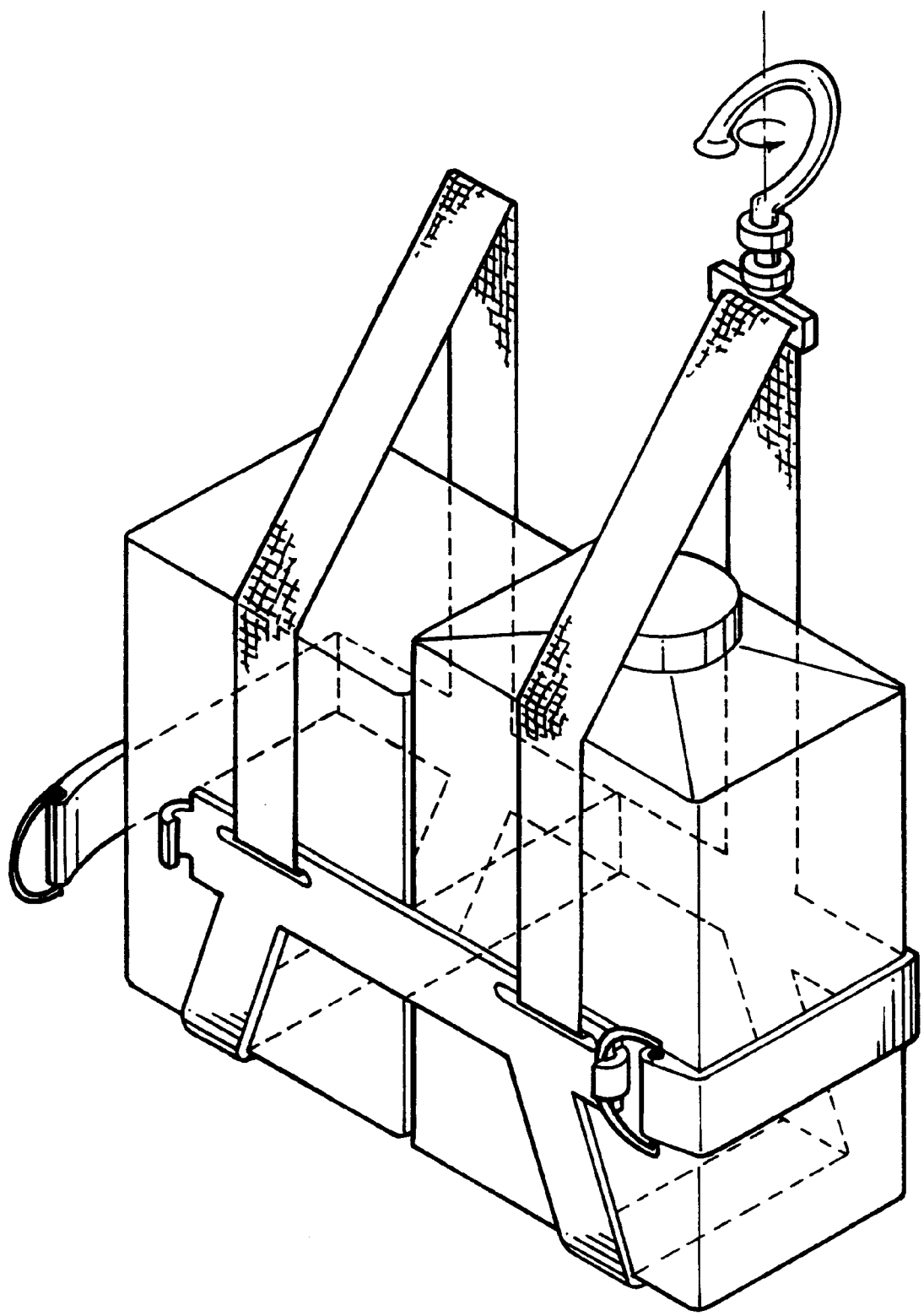

FIGS. 12 and 13 depict racks to hold the receptacle and pumps used in the present invention. The mounting hooks for the rack are preferably movable about an axis in a 360° range.

Figure 14:
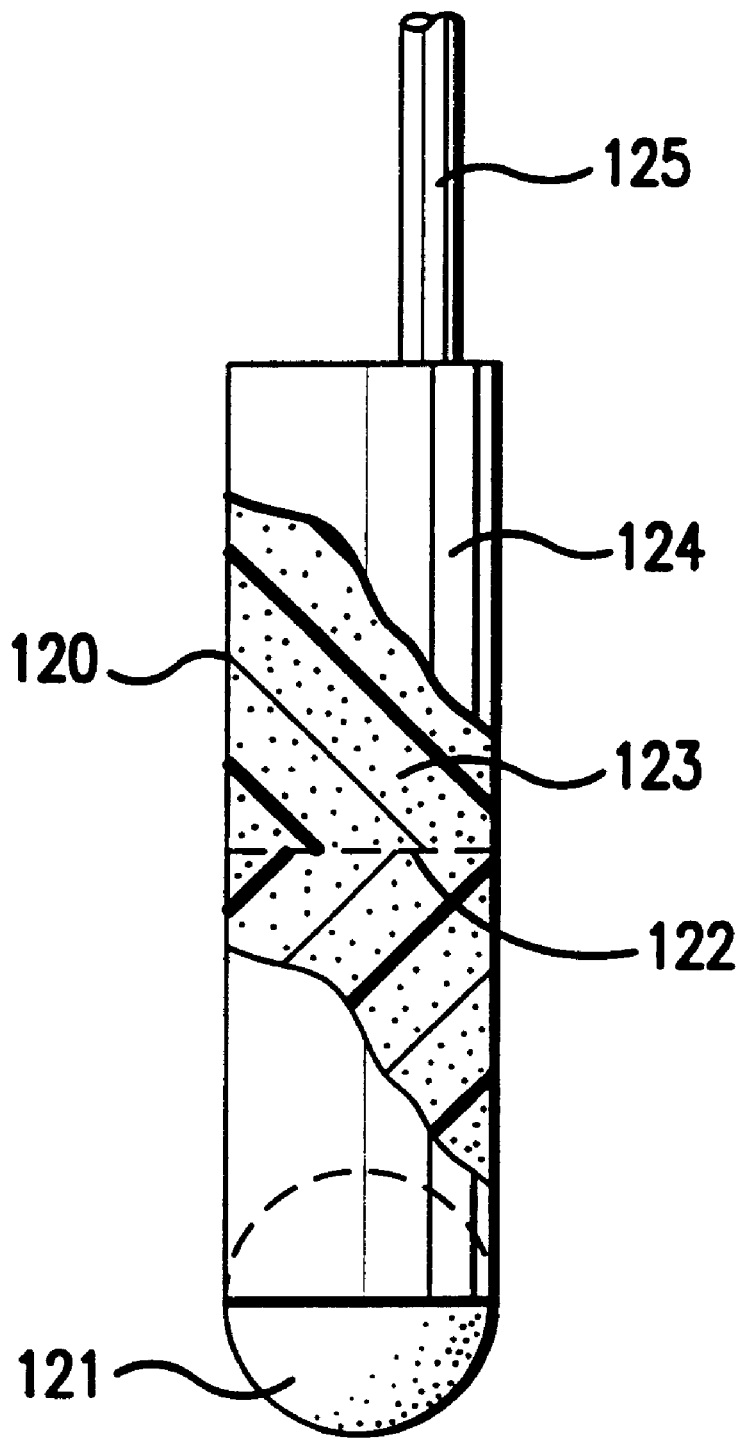
FIG. 14 depicts an interface device for use in liquid removal for use by a laboratory or work shop.

FIG. 14 depicts an interface device for general fluid removal operations such as in a laboratory or a workshop. The interface device comprises an absorbing means 120 which may be in a shape that is convenient to hold. Here it has been depicted as being round although other shapes and configurations are possible. A foam or fibrous material 121 protrudes from the device to permit the liquid to be absrbed by the interface device. Liquid passes through the foam and contacts the membrane 122. The vacuum on the opposite side of the membrane 123 causes the liquid to pass through the membrane, through foam material 124 and out the tubing 125.

We claim:

1. A liquid removal system which comprises an interface device, said interface device comprising a first zone and a second zone and having a porous membrane separating said first zone from said second zone, said second zone being adapted to be connected to a vacuum source, said porous membrane being capable of maintaining a vacuum in said second zone without permitting air from said first zone to pass through said membrane into said second zone when said membrane has been wetted with a first liquid; said vacuum being maintained until said membrane is contacted with a second liquid;

and wherein said second liquid upon entering said first zone and contacting said porous membrane is removed from said first zone by said vacuum in said second zone by passing through said membrane into said second zone.

2. A liquid removal system which comprises:

a) an interface device, said interface device having a body contact surface and a bottom surface said surfaces being connected to each other by means of upper and lower edges and a pair of side edges extending from said upper and lower edges, said interface device having a porous membrane connected to said edges and being separated from said surfaces, said porous membrane thereby forming an entrance zone and second zone in said interface device said porous membrane being capable of maintaining a vacuum in said second zone without permitting air from said entrance zone to pass through said membrane into said second zone when said membrane has been wetted with a first liquid; said vacuum being maintained until said membrane is contacted with a second liquid;

and wherein said second liquid upon entering said entrance zone and contacting said porous membrane is removed from said entrance zone by said vacuum in said second zone by passing through said membrane into said second zone.

3. The liquid removal system according to claim 2 wherein said side edges have concave surfaces.

4. The liquid removal system according to claim 2 wherein said second zone is connected to a vacuum source.

5. The liquid removal system according to claim 4 wherein said vacuum source comprises bag having a pair of drain tubes extending therefrom and a pair of check valves connected to said drain tubes, said bag having one or more springs therein.

6. The liquid removal system according to claim 4 wherein said vacuum source comprises a valve connected to one end of a T shaped tubing, said tubing having a second valve connected at a second end of said T shaped tubing and a pump connected to the third end of said T shaped tubing, said second valve being connected to a receptacle.

7. The liquid removal system according to claim 6 wherein said first and second valves are duck bill valves.

8. The liquid removal system according to claim 6 wherein said pump is a bellows.

9. The liquid removal system according to claim 4 wherein said pump is a peristaltic pump.

10. The liquid removal system according to claim 4 wherein said pump has a disposable pump head.

11. The liquid removal system according to claim 2 wherein first and second lengths of hollow tubing are connected to said second zone of said interface device at a first end of each of said tubing, said first length of tubing being connected to a vacuum bottle at the opposite end of said tubing and said second length of said tubing being connected at its opposite end to a pressure transducer, said system further comprising a third length of tubing extending from said second length of tubing to a pressure relief valve, said vacuum bottle being connected to a pump by a fourth length of tubing.

12. The liquid removal system according to claim 2 wherein first and second lengths of hollow tubing are connected to said second zone of said interface device at one end of each of said lengths of tubing, the first length of tubing being connected at its opposite end to a pressure relief valve, the second length of tubing being connected at its opposite end to a pump, said pump being connected to a collection bag and said pressure relief valve being separably connected to said collection bag.

13. The liquid removal system according to claim 2 adapted to be retained in place on a patient by retaining means.

14. The liquid removal system of claims 2 wherein said interface device is an external catheter.

15. A female catheter system which comprises a) an interface device, said interface device having a patient contact surface comprised of a flexible, fluid impervious material and being provided with an opening to receive urine, said interface device having a first zone and a second zone and having a porous membrane separating said first zone from said second zone, said first zone being capable of directing said urine to the porous membrane, said porous membrane being capable of supporting a vacuum in said second zone without permitting air from said entrance zone to pass through said membrane into said second zone when said membrane has been wetted with a first liquid, b) A vacuum source which is capable of maintaining a vacuum in said second zone until said membrane is contacted with urine, said vacuum source being capable of removing said urine from said interface device.

16. A female external catheter according to claim 15 wherein an open-surfaced, shape retaining material is in at least one of said first and second zones.

17. A female external catheter according to claim 16 wherein said open-surfaced, shape retaining material is an open celled reticulated foam.

18. A female external catheter according to claim 16 wherein said open-surfaced, shape retaining material is a wicking material.

19. A female external catheter according to claim 15 wherein said porous membrane has been wetted with glycerin.

20. A female external catheter according to claim 15 wherein said porous membrane has a pore size of about 5 to 30 microns.

21. A female external catheter according to claim 15 wherein said vacuum source comprises a pump.

22. A female external catheter according to claim 21 wherein said pump is connected to a pressure transducer which maintains a preselected vacuum.

23. A female external catheter according to claim 15 wherein said urine passes from said interface device to a vacuum bottle between said interface device and said pump.

24. A female external catheter according to claims 15 further comprising an external dam around said entrance zone.

25. A female external catheter according to claim 24 wherein said dam is comprised of a foam material.

26. A female external catheter according to claim 25 wherein said dam is contains a bump at the portion of the dam that contacts the region of the body between the anus and the vagina.

27. A method of removing liquid comprising a) Contacting the liquid with an interface device, said interface device comprising a first zone and a second zone and having a porous membrane separating said first zone from said second zone, said second zone having a vacuum source connected thereto b) Maintaining a vacuum in said second zone without permitting air from said first zone to pass through said membrane into said second zone when said membrane has been wetted with a second liquid, aid vacuum being maintained until said membrane is contacted with said first liquid.

c) passing said first liquid from said first zone through said porous membrane such that said first liquid is removed from said first zone.

28. The method according to claim 27 wherein said first liquid is urine.

29. The method according to claim 27 further comprising said porous membrane retaining liquid therein after said first liquid passes through said porous membrane such that said porous membrane remains capable of maintaining a vacuum in said second zone, without permitting air to enter said second zone through said porous membrane.

* * * * *